(12) United States Patent
Björck et al.

(10) Patent No.: US 8,133,483 B2
(45) Date of Patent: Mar. 13, 2012

(54) METHOD OF TREATING OR PREVENTING A DISEASE OR CONDITION MEDIATED BY PATHOGENIC IGG ANTIBODIES

(75) Inventors: Lars Björck, Lund (SE); Rikard Holmdahl, Lund (SE); Kutty Selva Nandakumar, Tamilnadu (IN)

(73) Assignee: Hansa Medical AB, Lund (SE)

( * ) Notice: Subject to any disclaimer, the term of this patent is extended or adjusted under 35 U.S.C. 154(b) by 993 days.

(21) Appl. No.: 11/921,770

(22) PCT Filed: Jun. 8, 2006

(86) PCT No.: PCT/EP2006/005454
§ 371 (c)(1),
(2), (4) Date: Apr. 11, 2008

(87) PCT Pub. No.: WO2006/131347
PCT Pub. Date: Dec. 14, 2006

(65) Prior Publication Data
US 2010/0303781 A1    Dec. 2, 2010

(30) Foreign Application Priority Data

Jun. 9, 2005 (GB) .................................. 0511769.2
Mar. 22, 2006 (GB) .................................. 0605781.4

(51) Int. Cl.
*A61K 38/48* (2006.01)
*C12N 9/52* (2006.01)
(52) U.S. Cl. ..................... 424/94.63; 424/800; 424/810; 435/220
(58) Field of Classification Search ............... 424/94.63, 424/800, 810; 435/220
See application file for complete search history.

(56) References Cited

FOREIGN PATENT DOCUMENTS
WO    03/051914    6/2003

OTHER PUBLICATIONS

Alwayn et al. The problem of anti-pig antibodies in pig-to-primate xenografting: current and novel methods of depletion and/or suppression of production of anti-pig antibodies. Xenotransplantation 1999: 6: 157-168.*
von Pawel-Rammingen et al. IdeS, a novel streptococcal cysteine proteinase with unique specificity for immunoglobulin G. The EMBO Journal vol. 21 No. 7 pp. 1607-1615, 2002.*
International Search Report for PCT/EP2006/005454 mailed Nov. 4, 2007.
Collin M. and Olsen A.; "Extracellular Enzymes with Immunomodulating Activities: Variation on a Theme in *Streptococcus pyogenes*", Infection and Immunity, vol. 71, No. 6, pp. 2983-2992, XP002426769, (Jun. 2003).
Schmaldienst et al, "Intravenous immunoglobulin application following immunoadsorption: benefit or risk in patients with autoimmune diseases?", Rheumatology 40:513-521 (2001).
Naparstek, "The Role of Autoantibodies in Autoimmune Disease", Annu. Rev. Immunol. 11:79-104 (1993).
Hickstein et al. "Autoimmune-associated Congenital Heart Block: Treatment of the Mother With Immunoadsorption", Therapeutic Apheresis and Dialysis, 9(2):148-153, Blackwell Publishing Inc. (2005).
Ismail et al. "Plasmapheresis", In: Daugirdas JT, Blake PG, Ing TS (eds), Handbook of Dialysis, 3rd ed. Lippincott Williams Wilkins, Philadelphia, pp. 231-262 (Chapter 11) (2001).
Matic et al. "Background and Indications for Protein A-Based Extracorporeal Immunoadsorption", Therapeutic Apheresis 5(5):394-403, Blackwell Science Inc. (2001).
Moldenhauer et al. Immunoadsorption patients with multiple sclerosis: an open-label pilot study, European Journal of Clinical Investigation 35: 523-530, Blackwell Publishing Ltd. (2005).
Hershko et al. "Removal of Pathogenic Autoantibodies by Immunoadsorption", Ann. N.Y. Acad. Sci. 1051: 635-646 (2005).
Samuelsson, G. "Extracorporeal Immunoadsorption With Protein A: Technical Aspects and Clinical Results", Journal of Clinical Apheresis 16:49-52 (2001).
Yang et al. "Successful treatment of experimental glomerulonephritis with IdeS and EndoS, IgG-degrading streptococcal enzymes", Nephrology Dialysis Transplantation, vol. 25, Issue 8, 2479-2486, Mar. 2010.
Johansson et al. "IdeS: A Bacterial Proteolytic Enzyme with Therapeutic Potential", PLOS One, vol. 3, Issue 2 Feb. 2008.
Tincani et al, "Induction of experimental SLE in naïve mice by Immunization with human polyclonal anti-DNA antibody carrying the 16/6 idiotype", Clinical and Experimental Rheumatology 11:129-134 (1993).
Nandakumar et al, "Induction of arthritis by single monoclonal IgG anti-collagen type II antibodies and enhancement of arthritis in mice lacking inhibitory FcγRIIB", Eur. J. Immunol. 33:2269-2277 (2003).
Schraa et al, "IgG, but not IgM, mediates hyperacute rejection in hepatic xenografting", Xenotransplantation 6:110-116 (1999).

* cited by examiner

*Primary Examiner* — Taeyoon Kim
(74) *Attorney, Agent, or Firm* — Nixon & Vanderhye P.C.

(57) ABSTRACT

The invention provides use of an IdeS polypeptide, or a polynucleotide encoding an IdeS polypeptide, in the manufacture of a medicament for the treatment or prevention of a disease or condition mediated by IgG antibodies.

13 Claims, 4 Drawing Sheets

METHOD OF TREATING OR PREVENTING A DISEASE OR CONDITION MEDIATED BY PATHOGENIC IGG ANTIBODIES

This application is the U.S. national phase of International Application No. PCT/EP2006/005454 filed 8 Jun. 2006 which designated the U.S. and claims priority to GB 0511769.2 filed 9 Jun. 2005 and GB 0605781.4 filed 22 Mar. 2006, the entire contents of each of which are hereby incorporated by reference.

FIELD OF THE INVENTION

The present invention relates to a method for treating or preventing diseases or conditions mediated by IgG antibodies, such as autoimmune diseases, transplant rejection, postoperative treatment and acquired haemophilia.

BACKGROUND OF THE INVENTION

IdeS (Immunoglobulin G-degrading enzyme of *S. pyogenes*) is an extracellular cysteine protease produced by the human pathogen *S. pyogenes*. IdeS was originally isolated from a group A streptococcal strain of serotype M1, but the ides gene has now been identified in all tested group A streptococcal strains. IdeS has an extraordinarily high degree of substrate specificity, with its only identified substrate being IgG. IdeS catalyses a single proteolytic cleavage in the lower hinge region of human IgG. This proteolytic degradation promotes inhibition of opsonophagocytosis and interferes with the killing of group A *Streptococcus*. IdeS also cleaves some subclasses of IgG in various animals and efficiently converts IgG into Fc and Fab fragments. The ides gene has been cloned and expressed in *E. coli* as a GST fusion protein.

SUMMARY OF THE INVENTION

The present inventors have shown that IdeS is useful in treating and preventing diseases mediated by IgG antibodies. In particular, the inventors have shown that IdeS can be used to treat rheumatoid arthritis (RA). IdeS administration to mice having induced rheumatoid arthritis had no observable toxic effect and completely prevented the development of rheumatoid arthritis. Furthermore, the inventors have shown that the effect of IdeS is highly potent and that IdeS has local effects.

In accordance with the present invention, there is thus provided the use of an IdeS polypeptide, or a polynucleotide encoding an IdeS polypeptide, in the manufacture of a medicament for the treatment or prevention of a disease or condition mediated by IgG antibodies.

The present invention also provides:
a method of treating or preventing a disease or condition mediated by IgG antibodies in a subject in need thereof, the method comprising administering to the subject a therapeutically effective amount of an IdeS polypeptide, or a polynucleotide encoding an IdeS polypeptide; and
a method of treating, ex vivo, blood taken from a patient suffering from a disease or condition mediated by IgG antibodies, comprising contacting the blood with an IdeS polypeptide.

BRIEF DESCRIPTION OF THE SEQUENCES

Figure 1:
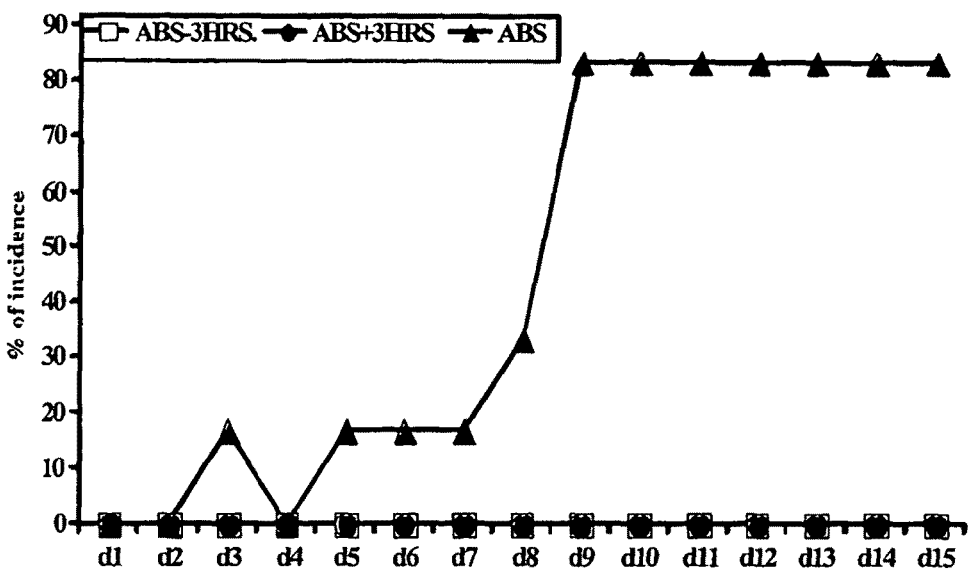
FIG. 1 shows the incidence (a) and severity (b) of arthritis in mice receiving IdeS and control mice. Time 0 is the injection of anti-CII antibodies. Mice were injected with IdeS (0.950 mg/mouse/i.v.) in PBS either 3 hours before (n=5) or after (n=5) the antibody transfer or without any treatment (n=6). On day 5, LPS (25 µg/mouse/i.p.) was injected to all the mice. Mice were monitored for arthritis development daily for 15 days. All the mice were used for calculations. n indicates the number of mice used in the experiments. Serum and paws were taken from the animals.
Figure 1:
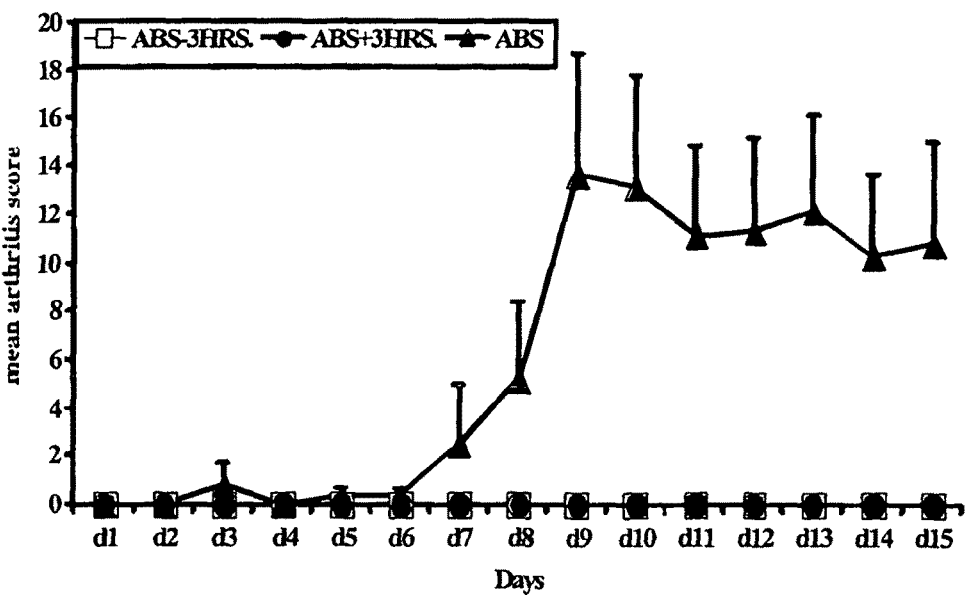

SEQ ID NO: 1 is an amino acid sequence encoding IdeS isolated from *S. pyogenes* AP1.

SEQ ID NO: 2 is an amino acid sequence encoding IdeS isolated from *S. pyogenes* AP1, including a putative signal sequence.

SEQ ID NO: 3 is a nucleic acid sequence encoding IdeS isolated from *S. pyogenes* AP1 (including a signal sequence).

SEQ ID NO: 4 is PCR primer Ide1.
SEQ ID NO: 5 is PCR primer Ide2.
SEQ ID NO: 6 is PCR primer Ide5x.
SEQ ID NO: 7 is PCR primer Ide3x.
SEQ ID NO: 8 is the N terminal amino acid sequence of an IdeS human IgG cleavage product.

DETAILED DESCRIPTION OF THE INVENTION

The present invention provides a method for treating or preventing diseases or conditions mediated by IgG antibodies, which method comprises administering to a subject an IdeS polypeptide or a polynucleotide encoding an IdeS polypeptide.

Polypeptides

The IdeS polypeptide is preferably *S. pyogenes* IdeS, or a variant or fragment of *S. pyogenes* IdeS which retains cysteine protease activity. The variant may be an IdeS polypeptide from another organism, such as another bacterium. The bacterium is preferably a *Streptococcus*. The *Streptococcus* is preferably a group A *Streptococcus*, a group C *Streptococcus* or a group G *Streptococcus*. In particular, the variant may be an IdeS polypeptide from a group C *Streptococcus* such as *S. quii* or *S. zooepidemicus*. Alternatively, the variant may be from *Pseudomonas putida*.

The IdeS polypeptide may comprise:
(a) the amino acid sequence of SEQ ID NO: 1;
(b) a variant thereof having at least 50% identity to the amino acid sequence of SEQ ID NO: 1 and having IgG cysteine protease activity; or
(c) a fragment of either thereof having IgG cysteine protease activity.

Preferably, the polypeptide comprises, or consists of, the sequence of SEQ ID NO: 1. The polypeptide may additionally include a signal sequence. Accordingly, the IdeS polypeptide may comprise:
(a) the amino acid sequence of SEQ ID NO: 2;
(b) a variant thereof having at least 50% identity to the amino acid sequence of SEQ ID NO: 2 and having IgG cysteine protease activity; or
(c) a fragment of either thereof having IgG cysteine protease activity.

The IdeS polypeptide may consist of the sequence shown in SEQ ID NO: 2.

Variant polypeptides are those for which the amino acid sequence varies from that in SEQ ID NO: 1 or SEQ ID NO: 2, but which retain the same essential character or basic functionality as IdeS. The variant polypeptides may therefore display IgG cysteine protease activity. Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 1 or SEQ ID NO: 2 are considered variants of the protein. Such variants may include allelic variants and the deletion, modification or addition of single amino acids or groups of amino acids within the protein sequence, as long as the peptide maintains the basic functionality of IdeS. The identity of variants of SEQ ID NO:1 or SEQ ID NO: 2 may be measured over a region of at least 50, at least 75, at least 100, at least 150, at least 200, at least 250, at least 275, at least 300 or more contiguous amino acids of the sequence shown in SEQ ID NO: 1 or SEQ ID NO: 2, or more preferably over the full length of SEQ ID NO: 1 or SEQ ID NO: 2.

Variants of the amino acid sequence of SEQ ID NO: 1 or SEQ ID NO: 2 preferably contain residues Lys-55 and/or Cys-65 and/or His-233 and/or Asp-255 and/or Asp-257 of SEQ ID NO: 1 (which correspond to Lys-84, Cys-94, His-262, Asp-284 and Asp-286 of SEQ ID NO: 2 respectively). Most preferably, the variant of SEQ ID NO: 1 or SEQ ID NO: 2 contains each of residues Lys-55, Cys-65, His-233, Asp-255 and Asp-257 of SEQ ID NO: 1 (which correspond to Lys-84, Cys-94, His-262, Asp-284 and Asp-286 of SEQ ID NO: 2 respectively)

Amino acid identity may be calculated using any suitable algorithm. For example the UWGCG Package provides the BESTFIT program which can be used to calculate homology (for example used on its default settings) (Devereux et al (1984) *Nucleic Acids Research* 12, 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant sequences typically differ by at least 1, 2, 5, 10, 20, 30, 50 or more mutations (which may be substitutions, deletions or insertions of amino acids). For example, from 1 to 50, 2 to 30, 3 to 20 or 5 to 10 amino acid substitutions, deletions or insertions may be made. The modified polypeptide generally retains activity as an IgG-specific cysteine protease. The substitutions are preferably conservative substitutions, for example according to the following Table. Amino acids in the same block in the second column and preferably in the same line in the third column may be substituted for each other:

| ALIPHATIC | Non-polar | G A P |
|---|---|---|
| | | I L V |
| | Polar - uncharged | C S T M |
| | | N Q |
| | Polar - charged | D E |
| | | K R |
| AROMATIC | | H F W Y |

It is possible to provide mutants of IdeS, in which mutation in the catalytic domain removes the cysteine protease activity of the protein. Such a mutant may comprise replacement or deletion of the catalytic cysteine residue at position 65 of SEQ ID NO: 1 (position 94 of SEQ ID NO: 2). For example, cysteine may be replaced with glycine. The invention also relates to variants of fragments of such a mutated IdeS, but which maintain the function of IdeS in displaying IgG cysteine protease activity.

Preferably the polypeptides comprise a cysteine residue and a histidine residue at a spacing typically found in cysteine proteases. For example, in SEQ ID NO: 1, these residues are found at a spacing of about 130 amino acids, as is typically found in cysteine proteases.

The fragment of the IdeS polypeptide used in the invention is typically at least 10, for example at least 15, 20, 25, 30, 40, 50 or more amino acids in length, up to 100, 150, 200, 250 or 300 amino acids in length, as long as it retains the IgG cysteine protease activity of IdeS. Preferably, the fragment of the IdeS polypeptide used in the invention encompasses residues Lys-55 and/or Cys-65 and/or His-233 and/or Asp-255 and/or Asp-257 of SEQ ID NO: 1 (which correspond to Lys-84, Cys-94, His-262, Asp-284 and Asp-286 of SEQ ID NO: 2 respectively). Most preferably, the fragment encompasses each of residues Lys-55, Cys-65, His-233, Asp-255 and Asp-257 of SEQ ID NO: 1 (which correspond to Lys-84, Cys-94, His-262, Asp-284 and Asp-286 of SEQ ID NO: 2 respectively).

The polypeptides used in the invention may be chemically modified, e.g. post-translationally modified. For example, they may be glycosylated, phosphorylated or comprise modified amino acid residues. They may be modified by the addition of histidine residues to assist their purification or by the addition of a signal sequence to promote insertion into the cell membrane. Such modified polypeptides fall within the scope of the term "polypeptide" used herein.

Typically, polypeptides for use in accordance with the invention display immunoglobulin cysteine protease activity, and in particular IgG cysteine protease activity. Preferably, the polypeptide cleaves IgG in the hinge region and more particularly in the hinge region of the heavy chain. Preferably, cleavage results in production of Fc and Fab fragments of IgG. Preferably the activity is specific for IgG. The cysteine protease activity may be determined by means of a suitable assay. For example, a test polypeptide may be incubated with IgG at a suitable temperature, such as 37° C. The starting materials and the reaction products may then be analysed by SDS PAGE to determine whether the desired IgG cleavage product is present. Typically this cleavage product is a 31 kDa fragment. Typically there is no further degradation of IgG after this first cleavage. The cleavage product may be subjected to N-terminal sequencing to verify that cleavage has occurred in the hinge region of IgG. Preferably the N-terminal sequence comprises the sequence in SEQ ID NO: 8.

The cysteine protease activity of the polypeptides can be further characterised by inhibition studies. Preferably, the activity is inhibited by the peptide derivate Z-LVG-$CHN_2$ and/or by iodoacetic acid both of which are protease inhibitors. However, the activity is generally not inhibited by E64.

The cysteine protease activity of the polypeptides is generally IgG-specific in that the polypeptides may not degrade the other classes of Ig, namely IgM, IgA, IgD and IgE, when incubated with these immunoglobulins under conditions that permit cleavage of IgG. The IdeS polypeptide is capable of cleaving IgG molecules present in the subject to be treated. Thus, where the subject is a human, the IdeS polypeptide is capable of cleaving human IgG. In preferred embodiments the polypeptide has the ability to cleave human, rabbit, mouse or goat IgG.

Polypeptides for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

Polypeptides for use in the present invention may be isolated from any suitable organism that expresses an IdeS polypeptide. Typically, the IdeS polypeptide is isolated from suitable IdeS expressing strains of *S. pyogenes*. Suitable organisms and strains may be identified by a number of techniques. For example, *S. pyogenes* strains may initially be tested for the presence an ides gene. Polynucleotide primers or probes may be designed based on for example, SEQ ID NOs: 1, 2 or 3. Examples of suitable primers are set out in SEQ ID NOs: 4, 5, 6 and 7. The presence of the ides gene can then be verified by PCR using the primers or by hybridisation of the probes to genomic DNA of the *S. pyogenes* strain.

*S. pyogenes* strains expressing active IdeS can be identified by assaying for IgG cysteine protease activity in the culture supernatant. Preferably inhibitor E64 is added to the supernatant to inhibit any SpeB cysteine protease activity. At least five strains express active IdeS: strains AP1, AP12, AP55, KTL3 and SF370. Preferably the expressing strain is selected from AP1, AP12 and AP55.

Isolation and purification of IdeS from an expressing *S. pyogenes* culture, or from cultures of other cells expressing IdeS is typically on the basis of IgG cysteine protease activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted polypeptides may then be subjected to ion exchange chromatography, for example by FPLC on a Mono Q column. Eluted fractions may be assayed for IgG cysteine protease activity and peak activity factions may be pooled. Fractions may be analysed by SDS PAGE. For example, an N-terminal sequence can be obtained from the SDS PAGE protein band. Fractions may be stored at −20° C.

Polypeptides for use in the invention may also be prepared as fragments of such isolated polypeptides. Further, the IdeS polypeptides may also be made synthetically or by recombinant means. For example, a recombinant IdeS polypeptide may be produced by transfecting mammalian cells in culture with an expression vector comprising a nucleotide sequence encoding the polypeptide operably linked to suitable control sequences, culturing the cells, extracting and purifying the IdeS polypeptide produced by the cells.

The amino acid sequence of polypeptides for use in the invention may be modified to include non-naturally occurring amino acids or to increase the stability of the compound. When the polypeptides are produced by synthetic means, such amino acids may be introduced during production. The polypeptides may also be modified following either synthetic or recombinant production.

Polypeptides for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the IdeS polypeptides, provided that the polypeptides retain IgG cysteine protease activity.

Polynucleotides

A polynucleotide encoding an IdeS polypeptide or variant may be used to treat or prevent a disease or condition mediated by pathogenic IgG antibiotics. In particular the polynucleotide may comprise or consist of: (a) the coding sequence of SEQ ID NO: 3; (b) a sequence which is degenerate as a result of the genetic code to the sequence as defined in (a); (c) a sequence having at least 60% identity to a sequence as defined in (a) or (b) and which encodes a polypeptide having IgG cysteine protease activity; or (d) a fragment of any one of the sequences as defined in (a), (b) or (c) which encodes a polypeptide having IgG cysteine protease activity.

Typically the polynucleotide is DNA. However, the polynucleotide may be a RNA polynucleotide. The polynucleotide may be single or double stranded, and may include within it synthetic or modified nucleotides.

A polynucleotide of the invention can typically hybridize to the coding sequence or the complement of the coding sequence of SEQ ID NO: 3 at a level significantly above background. Background hybridization may occur, for example, because of other DNAs present in a DNA library. The signal level generated by the interaction between a polynucleotide of the invention and the coding sequence or complement of the coding sequence of SEQ ID NO: 3 is typically at least 10 fold, preferably at least 100 fold, as intense as interactions between other polynucleotides and the coding sequence of SEQ ID NO: 3. The intensity of interaction may be measured, for example, by radiolabelling the probe, e.g. with $^{32}$P. Selective hybridisation may typically be achieved using conditions of medium to high stringency. However, such hybridisation may be carried out under any suitable conditions known in the art (see Sambrook et al, Molecular Cloning: A Laboratory Manual, 1989). For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 3 may be modified by nucleotide substitutions, for example from 1, 2 or 3 to 10, 25, 50 or 100 substitutions. The polynucleotide of SEQ ID NO: 3 may alternatively or additionally be modified by one or more insertions and/or deletions and/or by an extension at either or both ends. Additional sequences such as signal sequences may also be included. The modified polynucleotide generally encodes a polypeptide which has IgG specific cysteine protease activity. Degenerate substitutions may be made and/or substitutions may be made which would result in a conservative amino acid substitution when the modified sequence is translated, for example as shown in the Table above.

A nucleotide sequence which is capable of selectively hybridizing to the complement of the DNA coding sequence of SEQ ID NO: 3 will generally have at least 60%, at least 70%, at least 80%, at least 90%, at least 95%, at least 98% or at least 99% sequence identity to the coding sequence of SEQ ID NO: 3 over a region of at least 20, preferably at least 30, for instance at least 40, at least 60, more preferably at least 100 contiguous nucleotides or most preferably over the full length of SEQ ID NO: 3 or the length of SEQ ID NO: 3 encoding a polypeptide having the sequence shown in SEQ ID NO: 1. Sequence identity may be determined by any suitable method, for example as described above.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 20, preferably over 30 nucleotides forms one aspect of the invention, as does a polynucleotide which has at least 95% sequence identity over 40 nucleotides.

Polynucleotide fragments will preferably be at least 10, preferably at least 15 or at least 20, for example at least 25, at least 30 or at least 40 nucleotides in length. They will typically be up to 40, 50, 60, 70, 100 or 150 nucleotides in length. Fragments can be longer than 150 nucleotides in length, for example up to 200, 300, 400, 500, 600, 700, 800, 900 or 1000 nucleotides in length, or even up to a few nucleotides, such as five, ten or fifteen nucleotides, short of the coding sequence of SEQ ID NO: 3.

Polynucleotides for use in the invention may be produced recombinantly, synthetically, or by any means available to those of skill in the art. They may also be cloned by standard techniques. The polynucleotides are typically provided in isolated and/or purified form.

In general, short polynucleotides will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the ides gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. Suitable primers are for example, those in SEQ ID NOs: 4, 5, 6 or 7.

Such techniques may be used to obtain all or part of the ides gene sequence described herein. Although in general the techniques mentioned herein are well known in the art, reference may be made in particular to Sambrook et al. (1989).

IdeS polynucleotides as described herein have utility in production of the polypeptides for use in the present invention, which may take place in vitro, in vivo or ex vivo. The polynucleotides may be used as therapeutic agents in their own right or may be involved in recombinant protein synthesis.

The polynucleotides for use in the invention are typically incorporated into a recombinant replicable vector. The vector may be used to replicate the nucleic acid in a compatible host cell. Therefore, polynucleotides for use in the invention may be made by introducing an IdeS polynucleotide into a replicable vector, introducing the vector into a compatible host cell and growing the host cell under conditions which bring about replication of the vector.

Preferably the vector is an expression vector comprising a nucleic acid sequence that encodes an IdeS polypeptide. Such expression vectors are routinely constructed in the art of molecular biology and may for example involve the use of plasmid DNA and appropriate initiators, promoters, enhancers and other elements, such as for example polyadenylation signals, which may be necessary and which are positioned in the correct orientation in order to allow for protein expression. Other suitable vectors would be apparent to persons skilled in the art. By way of further example in this regard we refer to Sambrook et al. (1989).

Preferably, a polynucleotide for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vector is typically adapted to be used in vivo.

Promoters and other expression regulation signals may be selected to be compatible with the host cell for which expression is designed. Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector may further include sequences flanking the polynucleotide giving rise to polynucleotides which comprise sequences homologous to eukaryotic genomic sequences, preferably mammalian genomic sequences. This will allow the introduction of the polynucleotides of the invention into the genome of eukaryotic cells by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

Diseases and Conditions

The IdeS polypeptide, or polynucleotide, may be used to treat or prevent diseases or conditions mediated by pathogenic IgG antibodies. It is well known in the art that pathogenic IgG antibodies are involved in the pathogenesis of a number of different diseases and conditions. The present inventors have found that the role of pathogenic IgG antibodies in such diseases can be inhibited using an IdeS polypeptide or polynucleotide.

The disease or condition can be an autoimmune disease. Such diseases include Addison's disease, alopecia areata, ankylosing spondilitis, antiphospholipid syndrome, aplastic anaemia, autoimmune gastritis, autoimmune hearing loss, autoimmune haemolytic anaemias, autoimmune hepatitis, autoimmune hypoparathyroidism, autoimmune hypophysitis, autoimmune inner ear disease, autoimmune lymphoproliferative syndrome, autoimmune myocarditis, autoimmune oophoritis, autoimmune orchitis, autoimmune polyendocrinopathy, Beçhet's disease, bullous pemphigoid, cardiomyopathy, chronic inflammatory demyelinating polyneuropathy, Churg-Strauss syndrome, coeliac disease, Crohn's disease, CREST syndrome, Degos disease, epidermolysis bullosa acquisita, essential mixed cryoglobulinaemia, giant cells arteritis, glomerulonephritis, Goodpasture's syndrome, Graves' disease, Guillan-Barre syndrome, Hashimoto's thyroiditis, idiopathic thrombocytopenic purpura, inflammatory bowel disease, Kawasaki's disease, Meniere's syndrome, mixed connective tissue disease, Mooren's ulcer, multiple sclerosis, myasthenia gravis, pemphigus foliaceous, pemphigus vulgaris, pernicious anaemia, polyarteritis nodosa, polyglandular autoimmune syndrome type 1 (PAS-1), polyglandular autoimmune syndrome type 2 (PAS-2), polyglandular autoimmune syndrome type 3 (PAS-3), polymyositis/dermatomyositis, primary biliary cirrhosis, psoriasis, psoriatic arthritis, Raynaud's syndrome, Reiter's syndrome, rheumatoid arthritis, sarcoidosis, scleroderma, Sjögren's syndrome, subacute thyroiditis, sympathetic opthalmia, systemic lupus erythematosus, Takayasu's arteritis, type 1 diabetes mellitus, vitiligo, Vogt-Koyanagi-Harada disease or Wegener's granulomatosis. Preferably the autoimmune disease is rheumatoid arthritis (RA).

The disease or condition can be asthma. The asthma can be acute or chronic asthma.

IgG activates the classical pathway of the complement system. IdeS polypeptides and polynucleotides can therefore be used to treat diseases and conditions where complement activation is detrimental to the patient. For example, the IdeS polypeptides and polynucleotides can be used to treat transplantation-derived disorders, for example transplant rejection (such as allograft and xenograft rejection) and graft-versus-host disease. The transplantation-derived disorder may occur due to the transplantation of a tissue or an organ in a patient.

IdeS polypeptides and polynucleotides are also of use in post-operative treatment, for example in the treatment of patients who have undergone heart by-pass operations.

Further, IdeS polypeptides and polynucleotides can be used for the treatment of acquired haemophilia, i.e to remove IgG in haemophilia patients who have developed autoantibodies against coagulation factors.

The subject is typically a mammalian subject, such as a mouse, rat or primate (e.g. a marmoset or monkey). The subject may be human or a non-human animal. Where the subject is a laboratory animal such as a mouse, rat or primate, the animal may be treated to induce a disease or condition mediated by pathogenic IgG antibodies. For example, the mouse anti-CII antibody induced arthritis (CAIA) model described by Nandakumar et al. (Am. J. Pathol. 163(5): 1827-1837, 2003), or the modified version of that model described in the Examples, may be used.

Therapy and Prophylaxis

The present invention provides the use of IdeS polypeptides and polynucleotides to treat or prevent a disease or condition mediated by pathogenic IgG antibodies. Treatment may be therapeutic or prophylactic.

The IdeS polypeptide or polynucleotide may be administered to an individual in order to prevent the onset of one or more symptoms of the disease or condition. In this embodiment, the subject may be asymptomatic. The subject may have a genetic predisposition to the disease. A prophylactically effective amount of the polypeptide or polynucleotide is administered to such an individual. A prophylactically effective amount is an amount which prevents the onset of one or more symptoms of a disease or condition.

A therapeutically effective amount of the IdeS polypeptide or polynucleotide is an amount effective to ameliorate one or more symptoms of a disease or condition. Preferably, the individual to be treated is human.

The IdeS polypeptide or polynucleotide may be administered to the subject by any suitable means. The polypeptide or polynucleotide may be administered by enteral or parenteral routes such as via oral, buccal, anal, pulmonary, intravenous, intra-arterial, intramuscular, intraperitoneal, intraarticular, topical or other appropriate administration routes.

The IdeS polypeptide or polynucleotide may be administered to the subject in such a way as to target therapy to a particular site. For example, an IdeS polypeptide may be administered directly to the site of a transplanted organ. The IdeS polypeptide may be injected locally, for example intraarticularly or in one or more joints. Local administration of IdeS to the joints is particularly preferable for the prophylaxis or treatment of rheumatoid arthritis (RA). The IdeS polypeptide may be conjugated with reagents that bind cartilage specifically. For IdeS polynucleotides, expression vectors encoding the IdeS polypeptide may be used to direct expression of IdeS to a particular tissue, for example by using tissue-specific promoters or RNAi.

The formulation of any of the polypeptides and polynucleotides mentioned herein will depend upon factors such as the nature of the polypeptide or polynucleotide and the condition to be treated. The polypeptide or polynucleotide may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The polypeptide or polynucleotide may also be administered as suppositories. A physician will be able to determine the required route of administration for each particular patient.

Typically the polypeptide or polynucleotide is formulated for use with a pharmaceutically acceptable carrier or diluent and this may be carried out using routine methods in the pharmaceutical art. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Pharmaceutical compositions suitable for delivery by needleless injection, for example, transdermally, may also be used.

A therapeutically effective amount of polypeptide or polynucleotide is administered. The dose may be determined according to various parameters, especially according to the polypeptide or polynucleotide used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The IdeS nucleotide sequences described above and expression vectors containing such sequences can also be used as pharmaceutical formulations as outlined above. Preferably, the nucleic acid, such as RNA or DNA, in particular DNA, is provided in the form of an expression vector, which may be expressed in the cells of the individual to be treated. The vaccines may comprise naked nucleotide sequences or be in combination with cationic lipids, polymers or targeting systems. The vaccines may be delivered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 µg nucleic acid for particle mediated gene delivery and 10 µg to 1 mg for other routes.

The present invention also provides a method of treating, ex vivo, blood taken from a patient suffering from a disease or condition mediated by pathogenic IgG antibodies comprising contacting the blood with an IdeS polypeptide. IdeS may thus be used for extracorporeal treatment of blood. The IdeS may be used to treat one or more components of blood, such as plasma or serum. The ex vivo method described herein may be practised on blood that has already been removed from the body of a patient. The blood or blood product may optionally be returned to the patient after being contacted with an IdeS polypeptide.

The following Examples illustrate the invention:

EXAMPLE 1

Effect of IdeS on the Induction and Development of Arthritis

A uniquely designed animal model for rheumatoid arthritis (RA) was produced using mouse IgG2a antibodies reactive with type II collagen (CII), a variant of the anti-CII antibody induced arthritis (CAIA) model known from Nandakumar et al. (2003), to induce RA. Groups of male B10.RIII mice were i.v. transferred with 9 mg of CII specific IgG2a monoclonal antibody cocktail containing M287 and CIIC1 binding to J1 and C1$^{I}$ epitopes respectively. Mice were injected with IdeS (0.950 mg/mouse/i.v.) in PBS either 3 hours before (n=5) or after (n=5) the anti-CII antibody transfer. Control mice received no treatment (n=6). On day 5, LPS (25 μg/mouse/i.p.) was injected to all the mice. Mice were monitored for arthritis development daily for 15 days. Arthritis incidence (a) and severity (b) are indicated in FIG. 1. Survival and overall health of the animals were observed.

No mice died during the experiment or showed any adverse reactions after the treatment with IdeS. Except for the development of arthritis in the control group, the mice remained healthy. The results thus show that the IdeS treatment had no observable toxic effects and that it completely prevented the development of arthritis.

Figure 2:
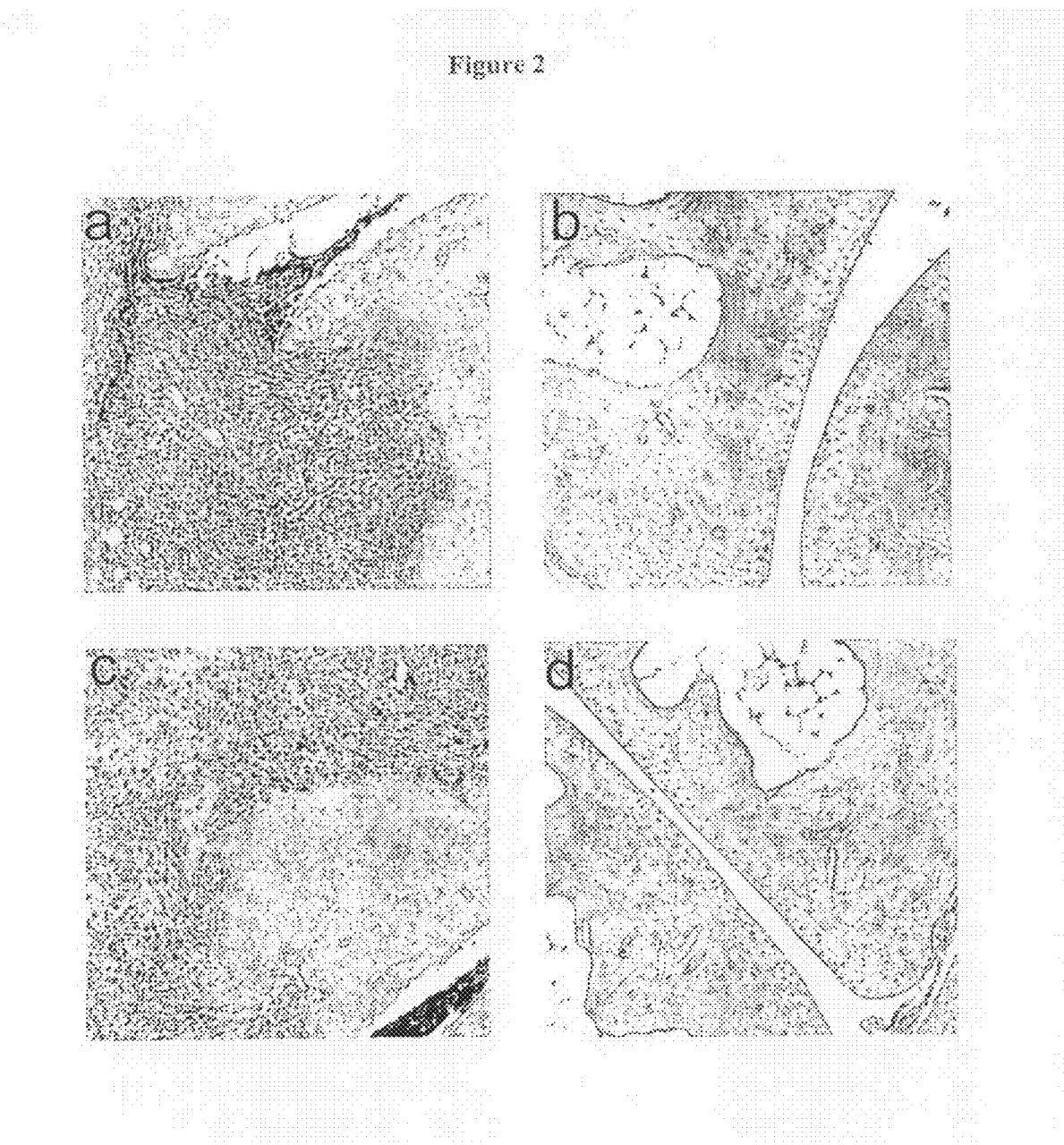
FIG. 2 shows histopathology sections of paws taken from control mice (a and c) and mice treated with IdeS as described for FIG. 1 (b and d). Mouse paws were collected on day 15 of the experiment. Hind paws were fixed in 4% phosphate buffered paraformaldehyde solution (pH 7.4) at 4° C. for 24 hours, decalcified for 4 weeks in an ethylenediaminetetraacetic acid solution containing polyvinypyrrolidone and 0.1M Tris (pH 6.95), dehydrated and embedded in paraffin. Sections of 6 µm were stained with hematoxylin and eosin. Results shown are representative of those obtained from three mice in each group. Original magnifications were ×20.

The sera will be analysed for levels of anti-CII antibodies. The paws were analysed for histology. The histology confirmed the clinical scoring data. FIG. 2 shows the histology of joint sections and infiltrated tissue surrounding the joints. In the control mice (a and c) there was an active inflammatory pannus tissue eroding bone and cartilage. In the treated mice (b and d) the joints were normal.

EXAMPLE 2

Determination of the Effective Dose of IdeS

To induce CAIA a cocktail of 9 mg of two monoclonal antibodies was used: (i) CIIC1 detecting the C1$^{I}$ epitope and of the IgG2a isotype; and (ii) M2139, detecting the J1 epitope and of the IgG2b isotype. Thus, the experiments differ from those conducted in Example 1 in that a different J1 specific antibody was used. The M2139 antibody has similar affinity for binding the J1 epitope as M287, used in Example 1. 3 hours after injection of the antibody cocktail into four month old male B10.RIII mice, the IdeS treatment was given at three different doses (10, 100 and 1000 μg). An untreated control group were given no IdeS (0 μg). As in Example 1, LPS was given on day 5 after injection of the antibody cocktail to enhance the development of arthritis.

Figure 3:
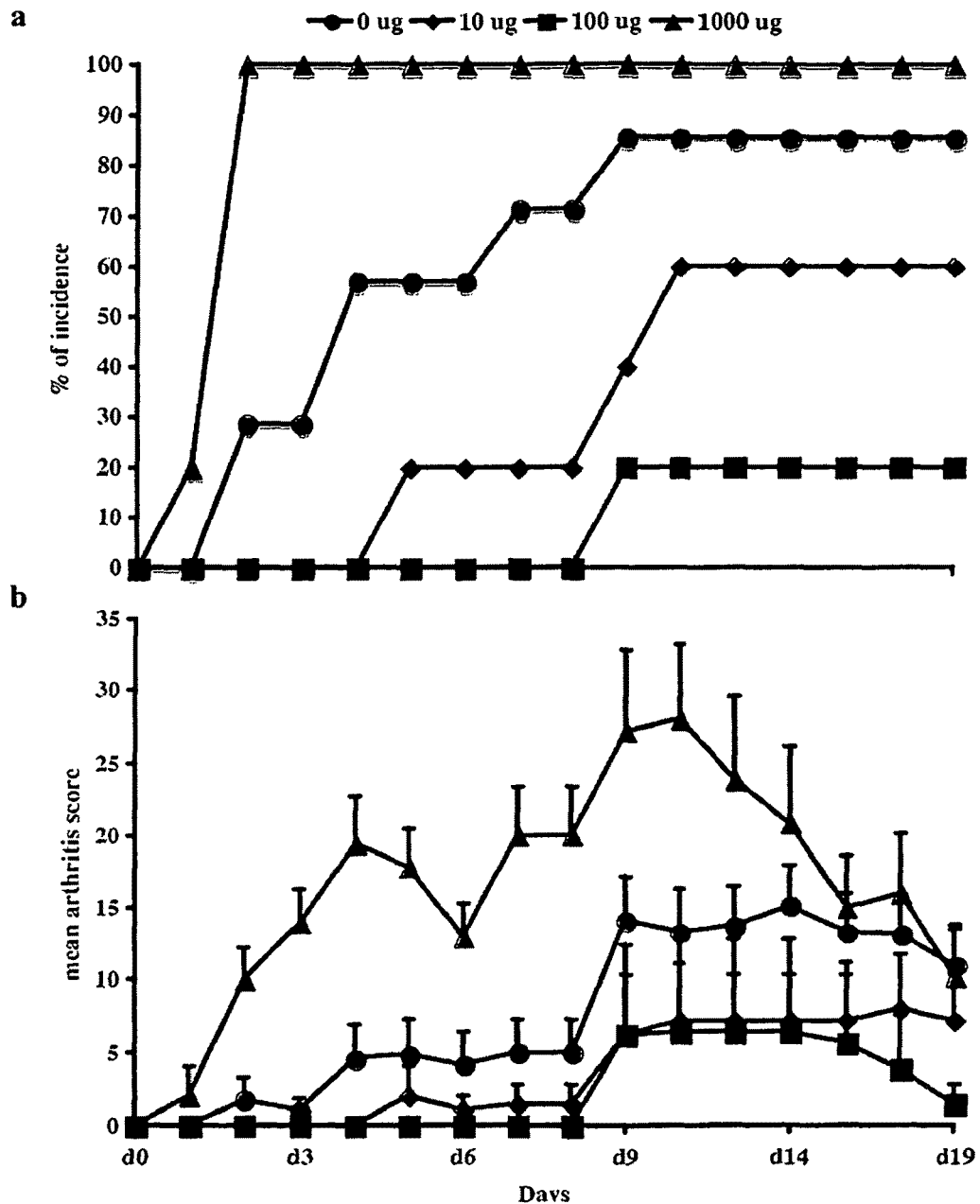
FIG. 3 shows the incidence (a) and severity (b) of arthritis in mice receiving various doses of IdeS and control mice. Groups of four month old male B10.RIII mice were injected i.v. with 9 mg of CII specific monoclonal antibodies, M2139 and CIIC1, at 0 hrs on day 0. After 3 hours on the same day 0 µg (n=7), 10 µg (n=5), 100 µg (n=5) and 1000 µg (n=5) of IdeS in PBS was injected i.v. On day 5, all the mice received LPS (25 ug/i.p.). n indicates number of mice in each group. Error bars indicate mean±SEM. All the mice were included for calculations.

Arthritis incidence (a) and severity (b) are indicated in FIG. 3. The Table below shows the incidence of arthritis at day 10.

| DAY 10: | (n arthritis/n total) |
|---|---|
| Untreated: | 6/7 |
| IdeS (1000 μg): | 5/5 |
| IdeS (100 μg): | 1/5 |
| IdeS (10 μg): | 2/5 |

The experiment was run to day 19 and essentially the same results were observed at day 19 (see FIG. 2).

It can be concluded from these results that:

a) The IdeS treatment is likely to be highly potent as there are clear effects at the lowest dose. The effective dose is lower than 100 μg. There is an effect with 10 μg but the more optimal effect is with 100 μg.

b) The lack of effect in the highest dose can possibly be explained by endotoxin contamination in the IdeS preparation.

EXAMPLE 3

Local Treatment of Arthritis Using IdeS

Figure 4:
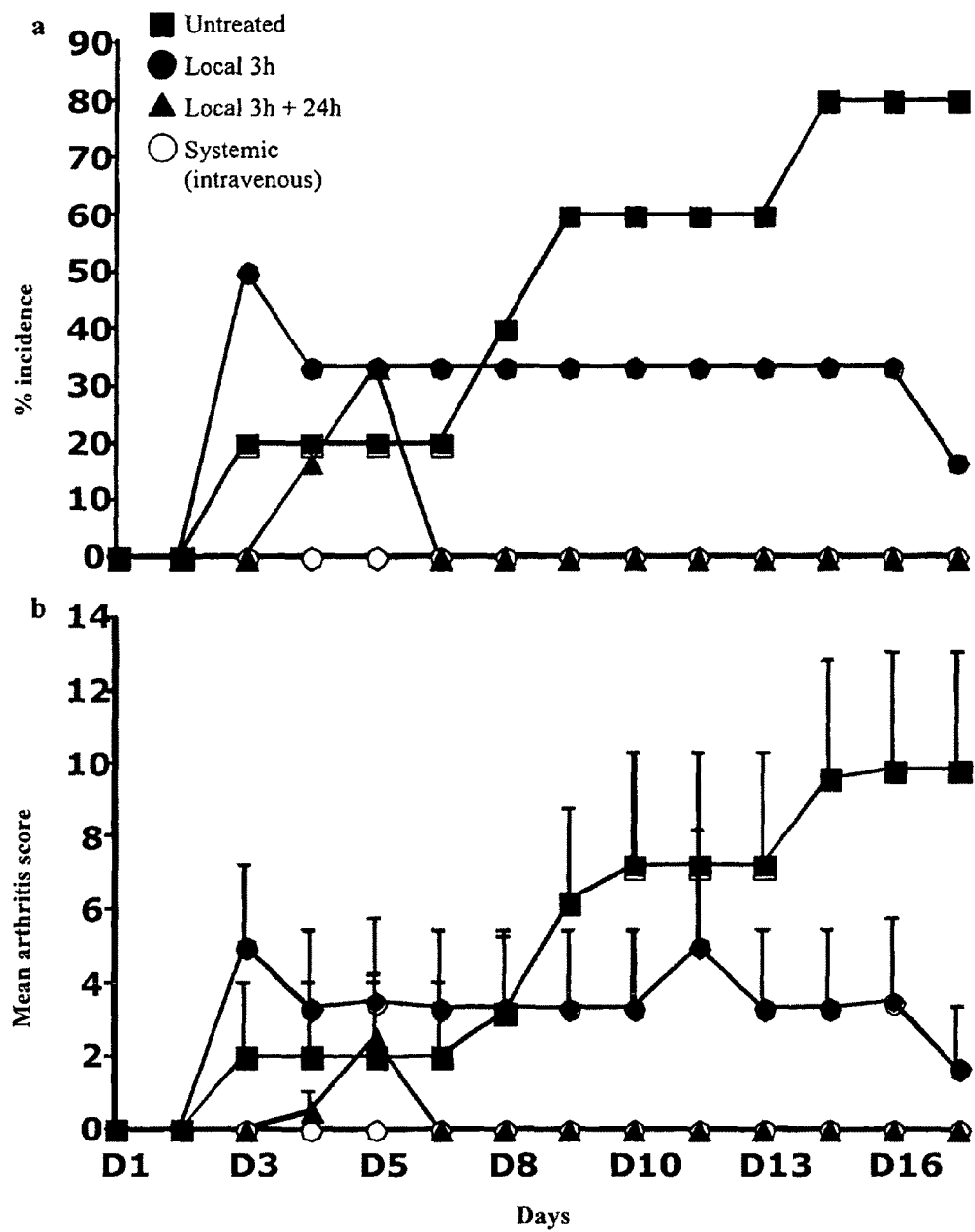
FIG. 4 shows the incidence (a) and severity (b) of arthritis in mice receiving IdeS systemically and locally and in control mice. Groups of B10.RIII mice were i.v. transferred with 9 mg of arthritogenic anti-CII IgG2a monoclonal antibody cocktail. Mice were treated with 100 µg of IdeS systemically (i.v.) (n=4) or locally (left or right paw). The mice treated locally were administered IdeS either 3 hours after the anti-CII antibody transfer (n=6) or 3 and 24 hours after the anti-CII antibody transfer (n=6).

Groups of B10.RIII mice were i.v. transferred with 9 mg of arthritogenic anti-CII IgG2a monoclonal antibody cocktail. Mice were treated with 100 μg of IdeS systemically (i.v.) (n=4) or locally (left or right paw). The mice treated locally were administered IdeS either 3 hours after the anti-CII antibody transfer (n=6) or 3 and 24 hours after the anti-CII antibody transfer (n=6). Arthritis incidence (a) and severity (b) are indicated in FIG. 4.

It can be concluded from these results that IdeS has local effects and is likely to degrade antibodies already bound to cartilage.

The invention claimed is:

1. A method of treating or preventing a disease or condition mediated by pathogenic IgG antibodies in a subject in need thereof, the method comprising administering to the subject a therapeutically effective amount of an Immunoglobulin G-degrading enzyme of S. pyogenes (IdeS) polypeptide, or a polynucleotide encoding an IdeS polypeptide, wherein said polynucleotide is incorporated in an expression vector.

2. The method according to claim 1, wherein said IdeS polypeptide comprises:

(a) the amino acid sequence of SEQ ID NO: 1;

(b) a variant thereof having at least 50% identity to the amino acid sequence of SEQ ID NO: 1 and having IgG cysteine protease activity; or (c) a fragment of either thereof having IgG cysteine protease activity.

3. The method according to claim 2, wherein said polypeptide consists of the sequence shown in SEQ ID NO: 1.

4. The method according to claim 1, wherein said polynucleotide comprises:
   (a) SEQ ID NO: 3;
   (b) a sequence having one or more degenerate substitutions relative to the sequence as defined in (a);
   (c) a sequence having at least 60% identity to a sequence as defined in (a) or (b) and which encodes a polypeptide having IgG cysteine protease activity; or
   (d) a fragment of any one of the sequences as defined in (a), (b) or (c) which encodes a polypeptide having IgG cysteine protease activity.

5. The method according to claim 4, wherein said polynucleotide consists of the nucleic acid sequence shown in SEQ ID NO: 3.

6. The method of claim 1, wherein the disease or condition mediated by pathogenic IgG antibodies is an autoimmune disease, transplant rejection or acquired haemophilia.

7. The method of claim 6, wherein said autoimmune disease is Addison's disease, alopecia areata, ankylosing spondilitis, antiphospholipid syndrome, aplastic anaemia, autoimmune gastritis, autoimmune hearing loss, autoimmune haemolytic anaemias, autoimmune hepatitis, autoimmune hypoparathyroidism, autoimmune hypophysitis, autoimmune inner ear disease, autoimmune lymphoproliferative syndrome, autoimmune myocarditis, autoimmune oophoritis, autoimmune orchitis, autoimmune polyendocrinopathy, Beçhet's disease, bullous pemphigoid, cardiomyopathy, chronic inflammatory demyelinating polyneuropathy, Churg-Strauss syndrome, coeliac disease, Crohn's disease, CREST syndrome, Degos disease, epidermolysis bullosa acquisita, essential mixed cryoglobulinaemia, giant cells arteritis, glomerulonephritis, Goodpasture's syndrome, Graves' disease, Guillan-Barre syndrome, Hashimoto's thyroiditis, idiopathic thrombocytopenic purpura, inflammatory bowel disease, Kawasaki's disease, Meniere's syndrome, mixed connective tissue disease, Mooren's ulcer, multiple sclerosis, myasthenia gravis, pemphigus foliaceous, pemphigus vulgaris, pernicious anaemia, polyarteritis nodosa, polyglandular autoimmune syndrome type 1 (PAS-1), polyglandular autoimmune syndrome type 2 (PAS-2), polyglandular autoimmune syndrome type 3 (PAS-3), polymyositis/dermatomyositis, primary biliary cirrhosis, psoriasis, psoriatic arthritis, Raynaud's syndrome, Reiter's syndrome, rheumatoid arthritis, sarcoidosis, scleroderma, Sjögren's syndrome, subacute thyroiditis, sympathetic opthalmia, systemic lupus erythematosus, Takayasu's arteritis, type 1 diabetes mellitus, vitiligo, Vogt-Koyanagi-Harada disease or Wegener's granulomatosis.

8. The method according to claim 7, wherein said autoimmune disease is rheumatoid arthritis.

9. The method according to claim 7, wherein said autoimmune disease is systemic lupus erythematosus.

10. The method according to claim 7, wherein said transplant rejection is allograft or xenograft rejection.

11. A method of treating, ex vivo, blood taken from a patient suffering from a disease or condition mediated by pathogenic IgG antibodies, comprising contacting the blood with an IdeS polypeptide.

12. The method according to claim 8, wherein the blood is returned to the patient after contacting it with said IdeS polypeptide.

13. The method according to claim 8, wherein the disease or condition is transplant rejection mediated by pathogenic IgG antibodies.

* * * * *

SEQUENCE LISTING

```
<160> NUMBER OF SEQ ID NOS: 8

<210> SEQ ID NO 1
<211> LENGTH: 310
<212> TYPE: PRT
<213> ORGANISM: Streptococcus pyogenes

<400> SEQUENCE: 1

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30
```

Phe Thr Gln Gly Glu Asp Val Phe His Ala Pro Tyr Val Ala Asn Gln
         35                  40                  45

Gly Trp Tyr Asp Ile Thr Lys Thr Phe Asn Gly Lys Asp Asp Leu Leu
 50                  55                  60

Cys Gly Ala Ala Thr Ala Gly Asn Met Leu His Trp Trp Phe Asp Gln
 65                  70                  75                  80

Asn Lys Asp Gln Ile Lys Arg Tyr Leu Glu Glu His Pro Gln Lys Gln
             85                  90                  95

Lys Ile Asn Phe Asn Gly Glu Gln Met Phe Asp Val Lys Glu Ala Ile
            100                 105                 110

Asp Thr Lys Asn His Gln Leu Asp Ser Lys Leu Phe Glu Tyr Phe Lys
            115                 120                 125

Glu Lys Ala Phe Pro Tyr Leu Ser Thr Lys His Leu Gly Val Phe Pro
        130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300

Ser Trp Asn Gln Thr Asn
305                 310

<210> SEQ ID NO 2
<211> LENGTH: 339
<212> TYPE: PRT
<213> ORGANISM: Streptococcus pyogenes

<400> SEQUENCE: 2

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
            20                  25                  30

Ser Ala Asn Gln Glu Ile Arg Tyr Ser Glu Val Thr Pro Tyr His Val
        35                  40                  45

Thr Ser Val Trp Thr Lys Gly Val Thr Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

```
Ala Thr Ala Gly Asn Met Leu His Trp Trp Phe Asp Gln Asn Lys Asp
                100                 105                 110

Gln Ile Lys Arg Tyr Leu Glu Glu His Pro Glu Lys Gln Lys Ile Asn
            115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 3
<211> LENGTH: 1020
<212> TYPE: DNA
<213> ORGANISM: Streptococcus pyogenes

<400> SEQUENCE: 3
atgagaaaaa gatgctattc aacttcagct gcagtattgg cagcagtgac tttatttgtt      60
ctatcggtag atcgtggtgt tatagcagat agttttctg ctaatcaaga gattagatat      120
tcggaagtaa caccttatca cgttacttcc gtttggacca aggagttac tcctccagca      180 aacttcactc aaggtgaaga tgtttttcac gctccttatg ttgctaacca aggatggtat      240
gatattacca aaacattcaa tggaaaagac gatcttcttt gcggggctgc cacagcaggg      300
aatatgcttc actggtggtt cgatcaaaac aaagaccaaa ttaaacgtta tttggaagag      360
catccagaaa agcaaaaaat aaacttcaat ggcgaacaga tgtttgacgt aaaagaagct      420
atcgacacta aaaccacca gctagatagt aaattatttg aatattttaa agaaaaagct      480
ttcccttatc tatctactaa acacctagga gttttccctg atcatgtaat tgatatgttc      540
attaacggct accgcttag tctaactaac cacggtccaa cgccagtaaa agaaggtagt      600
aaagatcccc gaggtggtat ttttgacgcc gtatttacaa gaggtgatca agtaagcta      660 ttgacaagtc gtcatgattt taagaaaaaa aatctcaaag aaatcagtga tctcattaag      720
```

```
aaagagttaa ccgaaggcaa ggctctaggc ctatcacaca cctacgctaa cgtacgcatc    780
aaccatgtta taaacctgtg gggagctgac tttgattcta acgggaacct taaagctatt    840
tatgtaacag actctgatag taatgcatct attggtatga agaaatactt tgttggtgtt    900
aattccgctg gaaaagtagc tatttctgct aaagaaataa aagaagataa tattggtgct    960
caagtactag ggttatttac actttcaaca gggcaagata gttggaatca gaccaattaa   1020

<210> SEQ ID NO 4
<211> LENGTH: 24
<212> TYPE: DNA
<213> ORGANISM: Artificial Sequence
<220> FEATURE:
<223> OTHER INFORMATION: Primer for PCR

<400> SEQUENCE: 4
cgttacttcc gtttggatcc aagg                                            24

<210> SEQ ID NO 5
<211> LENGTH: 26
<212> TYPE: DNA
<213> ORGANISM: Artificial Sequence
<220> FEATURE:
<223> OTHER INFORMATION: Primer for PCR

<400> SEQUENCE: 5
gaaatagcta cttctcgagc ggaatt                                          26

<210> SEQ ID NO 6
<211> LENGTH: 30
<212> TYPE: DNA
<213> ORGANISM: Artificial Sequence
<220> FEATURE:
<223> OTHER INFORMATION: Primer for PCR

<400> SEQUENCE: 6
tcggtagatc gtgggatcct agcagatagt                                      30

<210> SEQ ID NO 7
<211> LENGTH: 28
<212> TYPE: DNA
<213> ORGANISM: Artificial Sequence
<220> FEATURE:
<223> OTHER INFORMATION: Primer for PCR

<400> SEQUENCE: 7
cggaattctt aattggtctg attccaac                                        28

<210> SEQ ID NO 8
<211> LENGTH: 8
<212> TYPE: PRT
<213> ORGANISM: Homo sapiens

<400> SEQUENCE: 8

Gly Pro Ser Val Phe Leu Phe Pro
 1               5
```